US008008265B2

(12) United States Patent
Weiner et al.

(10) Patent No.: US 8,008,265 B2
(45) Date of Patent: Aug. 30, 2011

(54) VACCINES, IMMUNOTHERAPEUTICS AND METHODS FOR USING THE SAME

(75) Inventors: David B. Weiner, Merion, PA (US); Karuppiah Muthumani, Cherry Hill, NJ (US); Michele Kutzler, Souderton, PA (US); Andrew Y. Choo, Brighton, MA (US); Michael A. Chattergoon, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 877 days.

(21) Appl. No.: 10/560,653

(22) PCT Filed: Jun. 14, 2004

(86) PCT No.: PCT/US2004/019028
§ 371 (c)(1),
(2), (4) Date: Nov. 20, 2006

(87) PCT Pub. No.: WO2004/112706
PCT Pub. Date: Dec. 29, 2004

(65) Prior Publication Data
US 2007/0104686 A1 May 10, 2007

Related U.S. Application Data

(60) Provisional application No. 60/478,187, filed on Jun. 13, 2003, provisional application No. 60/478,250, filed on Jun. 13, 2003, provisional application No. 60/478,230, filed on Jun. 13, 2003.

(51) Int. Cl.
*A61K 48/00* (2006.01)
*A61K 38/00* (2006.01)
(52) U.S. Cl. .................. 514/44; 424/229.1; 424/93.1
(58) Field of Classification Search ............... 435/320.1; 544/44; 514/44; 424/93.1
See application file for complete search history.

(56) References Cited

U.S. PATENT DOCUMENTS

| 4,722,848 A | 2/1988 | Paoletti et al. |
| 4,945,050 A | 7/1990 | Sanford et al. |
| 5,017,487 A | 5/1991 | Stunnenberg et al. |
| 5,036,006 A | 7/1991 | Sanford et al. |
| 5,077,044 A | 12/1991 | Stocker |
| 5,110,587 A | 5/1992 | Paoletti et al. |
| 5,112,749 A | 5/1992 | Brey |
| 5,174,993 A | 12/1992 | Paoletti |
| 5,223,424 A | 6/1993 | Cochran |
| 5,225,336 A | 7/1993 | Paoletti |
| 5,240,703 A | 8/1993 | Cochran |
| 5,242,829 A | 9/1993 | Panicali |
| 5,294,441 A | 3/1994 | Curtiss |
| 5,294,548 A | 3/1994 | McInden |
| 5,310,668 A | 5/1994 | Ellis |
| 5,387,744 A | 2/1995 | Curtiss |
| 5,389,368 A | 2/1995 | Curtiss |
| 5,424,065 A | 6/1995 | Curtiss |
| 5,451,499 A | 9/1995 | Cochran |
| 5,453,364 A | 9/1995 | Paoletti |
| 5,462,734 A | 10/1995 | Letchworth |
| 5,470,734 A | 11/1995 | Sondermeijer |
| 5,482,713 A | 1/1996 | Paoletti |
| 5,580,859 A | 12/1996 | Felgner |
| 5,593,972 A | 1/1997 | Weiner |
| 5,676,594 A | 10/1997 | Joosten |
| 5,703,055 A | 12/1997 | Felgner |
| 5,739,118 A | 4/1998 | Carrano |
| 5,817,634 A | 10/1998 | Meezan |
| 5,830,876 A | 11/1998 | Weiner |
| 5,962,425 A | 10/1999 | Walder |
| 5,981,505 A | 11/1999 | Weiner |
| 6,017,735 A * | 1/2000 | O'Hare et al. ............... 435/69.7 |
| 6,344,445 B1 * | 2/2002 | Boursnell et al. ............ 514/44 R |
| 2002/0044941 A1 * | 4/2002 | Rosen et al. ................ 424/184.1 |
| 2003/0113919 A1 * | 6/2003 | Emtage et al. ................ 435/456 |

FOREIGN PATENT DOCUMENTS

| JP | 2002-504334 | 2/2002 |
| WO | WO 94/16737 | 8/1994 |
| WO | WO 98/44129 | 10/1998 |
| WO | WO 99/42585 | 8/1999 |
| WO | WO 02/100345 | 12/2002 |

OTHER PUBLICATIONS

Kruse et al. Proc. Natl. Acad. Sci. USA, 1997, vol. 94, pp. 12396-12400.*
Kerppola et al. EMBO J. 1997, vol. 16 (10), pp. 2907-2916.*
Zhan et al. DNA and Cell Biology, 2000, vol. 19, No. 11, pp. 637-645.*
Taylor et al. J. Leukocyte Biology Sep. 2002, vol. 72, pp. 522-529.*
Song et al. Mol Biol Cell. Mar. 2004; 15(3): 1287-1296.*
Hodge et al. .JNCI 2000, vol. 92, No. 15, pp. 1228-1239.*
Hinuma et al. FEBS 1991, vol. 288, No. 1-2, pp. 138-142.* Wiethe, C et al., "Enhanced Effector and Memory CTL Responses Generated by Incorporation of Receptor Activator of NF-k (RANK)/RANK Ligand Costimulatory Molecules into Dendritic Cell Immunogens Expressing a Human Tumor-Specific Antigen," The Journal of Immunology (2003) 171(8):4121-30.
Hurwitz, A. et al., "Costimulatory wars: the tumor menace," Current Opinion in Immunology (2000) 12(5):589-596.
Wiethe, C. et al., "Provision of 4-1BB ligand enhances effector and memory CTL responses generated by immunization with dendritic cells expressing a human tumor-associated antigen", Journal of Immunology, 2003, 170 (6):2912-2922.
Zheng, J. et al., "Enhanced immune response to DNA-based HPV16L1 vaccination by costimulatory molecule B7-2", Antiviral Research, 2003:59(1):61-65.

(Continued)

*Primary Examiner* — Bao Li
(74) *Attorney, Agent, or Firm* — Pepper Hamilton LLP

(57) ABSTRACT

Compositions, recombinant vaccines and live attenuated pathogens comprising one or more isolated nucleic acid molecules that encode an immunogen in combination with an isolated nucleic acid molecule that encodes an immunomodulator protein selected from the group consisting of: Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof are disclosed. Methods of inducing an immune response in an individual against an immunogen, using such compositions are disclosed.

6 Claims, 2 Drawing Sheets

OTHER PUBLICATIONS

Chaudhary, V.K., et al., "A rapid method of cloning functional variable-region antibody genes in *Escherichia coli* as single-chain immunotoxins," *Proc. Natl. Acad Sci. USA* (1990) 87(3):1066-70.

Chiu et al., "The c-Fos protein interacts with c-Jun/AP-1 to stimulate transcription of AP-1 responsive genes," *Cell* (1988) 54(2):541-552.

Durkop, H et al., "Molecular cloning and expression of a new member of the nerve growth factor receptor family that is characteristic for Hodgkin's disease," *Cell* (1992) 68(3),421-427.

Franklin et al., "Constitutively active MAP kinase kinase (MEK1) stimulates SAP kinase and c-Jun transcriptional activity in U937 human leukemic cells," *Oncogene* (1995) 11(11):2365-74.

Gilmore et al., "The I kappa B proteins: members of a multifunctional family," *Trens Genet* (1993) 9(12):427-33.

Howell, M.D., et al., "Limited T-cell receptor beta-chain heterogeneity among interleukin 2 receptor-positive synovial T cells suggests a role for superantigen in rheumatoid arthritis.," *Proc. Nat. Acad. Sci USA*. (1991) 88:10921-10925.

Lee et al., "Purified transcription factor AP-1 interacts with TPA-inducible enhancer elements," *Cell* (1987) 49(6):741-752.

Meyer R., et al., "Cloning of the DNA-binding subunit of human nuclear factor kappa B: the level of its mRNA is strongly regulated by phorbol ester or tumor necrosis factor alpha.," *Proc. Natl. Acad. Sci USA* (1991) 88(3),966-970.

Oksenberg, J.R., et al., "Limited heterogeneity of rearranged T-cell receptor Vα transcripts in brains of multiple sclerosis patients, "*Nature* (1990) 345(6264):344-346.

Paliard, X., et al., "Evidence for the effects of a superantigen in rheumatoid arthritis., " *Science* (1991) 253(5017):325-329.

Rauscher et al., "Fos-associated protein p39 is the product of the jun proto-oncogene," *Science* (1988) 240(4855):1010-1016.

Smith, C.A., et al., "CD30 antigen, a marker for Hodgkin's lymphoma, is a receptor whose ligand defines an emerging family of cytokines with homology to TNF," *Cell* (1993) 73(7):1349-1360.

Williams, W.V., et al., "Restricted heterogeneity of T cell receptor transcripts in rheumatoid synovium.," *J Clin. Invest.* (1992) 90(2):326-333.

Wucherpfennig, K.W., et al., "Shared human T cell receptor V beta usage to immunodominant regions of myelin basic protein.," *Science* (1990) 248(4958):1016-1019.

Murakami, M. "High-level expression of exogenous genes by replication-competent retrovirus vectors with an internal ribosomal entry site." *Gene* (1997) 202:23-29.

Clement, A. et al., Prime-boost immunization with DNA and modified vaccine virus Ankara vector expressing herpes simplex virus-2 glycoprotein d elicits create specific antibody and cytokine responses than DNA vaccine alone, J. Infectious Dis. 2001, vol. 186. pp. 1065-1073.

Luo, Y. et al., "Transcription factor Fos-related antigen 1 is an effective target for a breast cancer vaccine." *PNAS* (2003) 100; 8850-8855.

Stuber, E. et al., "Cross -Linking of OX40 Ligand, a Member of the TNF/NGF Cytokine Family, Induces Proliferation and Differentiation in Murine Splenic B Cells", Immunity, 1995, 2:507-521.

\* cited by examiner

Enhanced antibody and CD4+ responses seen with coadministration of plasmid-encoded OX40
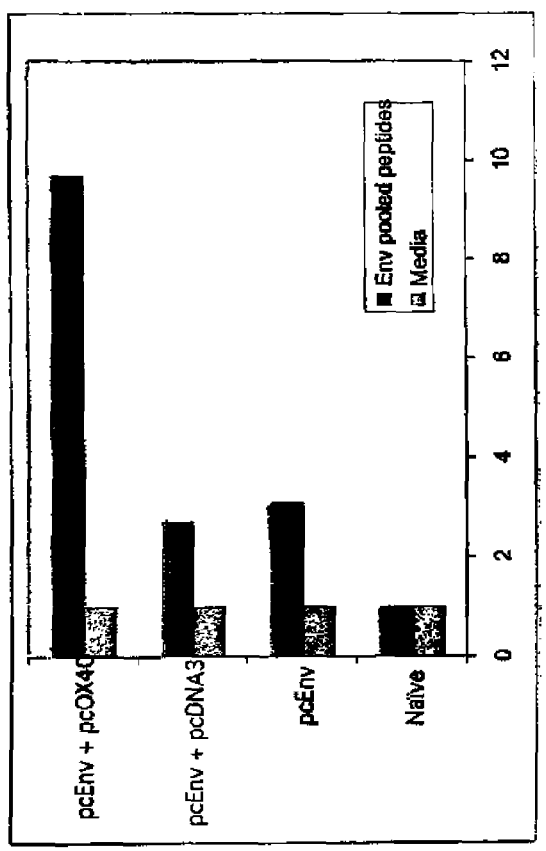
Figure 2: CD4 T cell Lymphocyte Proliferation Assay in response to HIV env immunization with coadministration of OX40
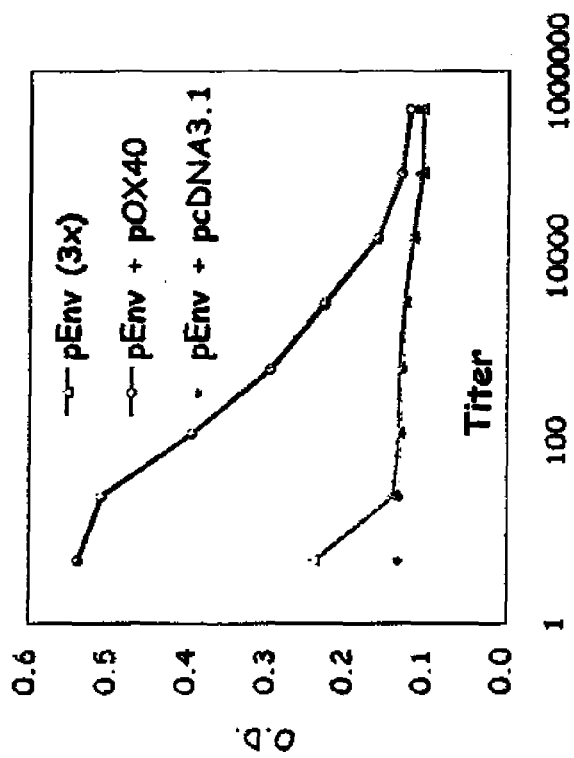
Figure 1: Antibody titers of of balb/c mice to HIV env with coadministration of OX40

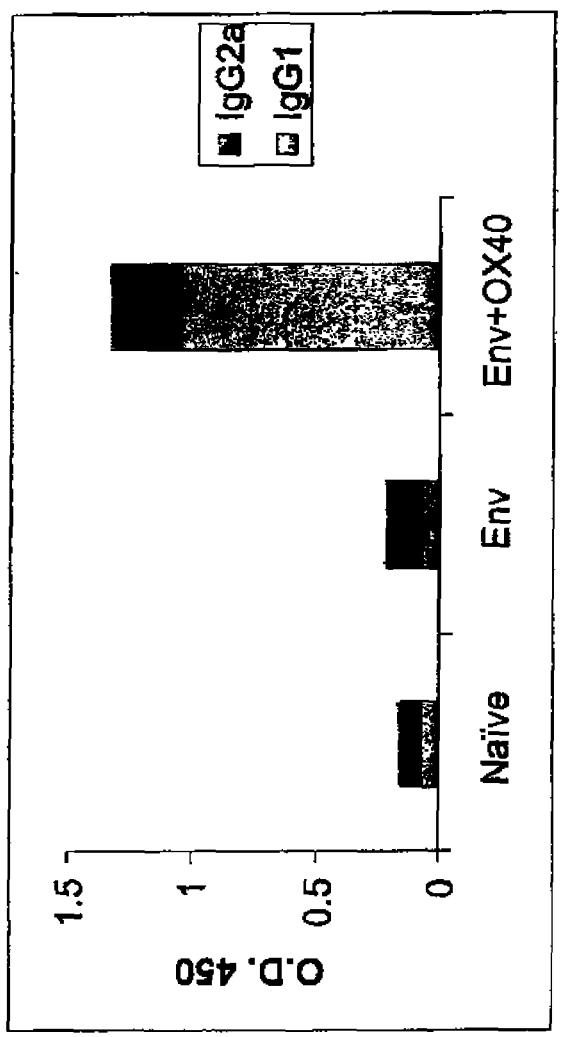
Figure 3: Response of C57BL6 HLA-DR transgenic mice to HIV env with coadministration of OX40 (at 1:1,000 dilution)

VACCINES, IMMUNOTHERAPEUTICS AND METHODS FOR USING THE SAME

CROSS-REFERENCE TO RELATED APPLICATIONS

This application is a national stage application of PCT International Application PCT/US2004/019028, filed Jun. 14, 2004, which claims priority to U.S. Provisional Patent Applications 60/478,187, filed Jun. 13, 2003; 60/478,250, filed Jun. 13, 2003; and 60/478,230, filed Jun. 13, 2003.

FIELD OF THE INVENTION

The present invention relates to improved vaccines, improved methods for prophylactically and/or therapeutically immunizing individuals against immunogens, and to improved immunotherapeutic compositions and improved immunotherapy methods.

BACKGROUND OF THE INVENTION

Immunotherapy refers to modulating a person's immune responses to impart a desirable therapeutic effect. Immunotherapeutics refer to those compositions which, when administered to an individual, modulate the individual's immune system sufficient to ultimately decrease symptoms which are associated with undesirable immune responses or to ultimately alleviate symptoms by increasing desirable immune responses. In some cases, immunotherapy is part of a vaccination protocol in which the individual is administered a vaccine that exposes the individual to an immunogen against which the individual generates an immune response in such cases, the immunotherapeutic increases the immune response and/or selectively enhances a portion of the immune response (such as the cellular arm or the humoral arm) which is desirable to treat or prevent the particular condition, infection or disease.

Vaccine protocols can be improved by the delivery of agents that modulate a person's immune responses to induce an improved immune response. In some vaccination protocols in which the individual is administered a vaccine that exposes the individual to an immunogen against which the individual generates an immune response, an agent is provided that increases the immune response and/or selectively enhances a portion of the immune response (such as the cellular arm or the humoral arm) which is desirable to treat or prevent the particular condition, infection or disease.

Vaccines are useful to immunize individuals against target antigens such as allergens, pathogen antigens or antigens associated with cells involved in human diseases. Antigens associated with cells involved in human diseases include cancer-associated tumor antigens and antigens associated with cells involved in autoimmune diseases.

In designing such vaccines, it has been recognized that vaccines that produce the target antigen in cells of the vaccinated individual are effective in inducing the cellular arm of the immune system. Specifically, live attenuated vaccines, recombinant vaccines which use avirulent vectors, and DNA vaccines each lead to the production of antigens in the cell of the vaccinated individual which results in induction of the cellular arm of the immune system On the other hand, killed or inactivated vaccines, and sub-unit vaccines which comprise only proteins do not induce good cellular immune responses although they do induce a humoral response.

A cellular immune response is often necessary to provide protection against pathogen infection and to provide effective immune-mediated therapy for treatment of pathogen infection, cancer or autoimmune diseases. Accordingly, vaccines that produce the target antigen in cells of the vaccinated individual such as live attenuated vaccines, recombinant vaccines that use avirulent vectors and DNA vaccines are often preferred.

While such vaccines are often effective to immunize individuals prophylactically or therapeutically against pathogen infection or human diseases, there is a need for improved vaccines. There is a need for compositions and methods that produce an enhanced immune response.

Likewise, while some immunotherapeutics are useful to modulate immune response in a patient there remains a need for improved immunotherapeutic compositions and methods.

SUMMARY OF THE INVENTION

The present invention relates to a composition an isolated nucleic acid molecule that encodes an immunogen in combination with an isolated nucleic acid molecule that encodes a transcription factor selected from the group consisting of: Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The present invention further relates to a composition an isolated nucleic acid molecule that encodes both an immunogen and a transcription factor selected from the group consisting of: Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The present invention relates to injectable pharmaceutical compositions comprising an isolated nucleic acid molecule that encodes an immunogen in combination with an isolated nucleic acid molecule that encodes one or more transcription factors selected from the group consisting of: Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The present invention relates to injectable pharmaceutical compositions comprising an isolated nucleic acid molecule that encodes both an immunogen and one or more transcription factors selected from the group consisting of: Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The present invention further relates to methods of inducing an immune response in an individual against an immunogen, comprising administering to the individual a composition an isolated nucleic acid molecule that encodes an immunogen in combination with an isolated nucleic acid molecule that encodes one or more transcription factors selected from the group consisting of: Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The present invention further relates to methods of inducing an immune response in an individual against an immunogen, comprising administering to the individual a nucleic acid molecule that encodes an immunogen and one or more transcription factors selected from the group consisting of: Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The present invention further relates to recombinant vaccines comprising a nucleotide sequence that encodes an immunogen operably linked to regulatory elements, a nucleotide sequences that encode one or more transcription factors selected from the group consisting of: Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof, and to methods of inducing an immune response in an individual against an immunogen comprising administering such a recombinant vaccine to an individual.

The present invention further relates to a live attenuated pathogen, comprising a nucleotide sequence that encodes one or more transcription factors selected from the group consisting of: Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof, and to methods of inducing an immune response in an individual against a pathogen comprising administering the live attenuated pathogen to an individual.

BRIEF DESCRIPTION OF THE FIGURES

FIG. 1 shows antibody titers of balb/c mice to HIV env with and without co-administration of OX40.

FIG. 2 shows data from CD4 T cell lymphocyte proliferation assays.

FIG. 3 shows responses of C57B6 HLA-DR transgenic mice to HIV env with coadmininstration of OX40 at 1:1,000 dilution.

DETAILED DESCRIPTION OF PREFERRED EMBODIMENTS

As used herein, the term "immunomodulating proteins" is meant to refer to one or more transcription factors selected from the group consisting of Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

As used herein, "functional fragment" is meant to refer to a fragment of an immunomodulating protein that, when delivered in conjunction with an immunogen, provides an increased immune response compared to the immune that is induced when the immunogen is delivered without the fragment. Fragments are generally 10 or more amino acids in length.

As used herein the term "target protein" is meant to refer to peptides and protein encoded by gene constructs of the present invention that act as target proteins for an immune response. The terms "target protein" and "immunogen" are used interchangeably and refer to a protein against which an immune response can be elicited. The target protein is an immunogenic protein that shares at least an epitope with a protein from the pathogen or undesirable cell-type such as a cancer cell or a cell involved in autoimmune disease against which an immune response is desired. The immune response directed against the target protein will protect the individual against and/or treat the individual for the specific infection or disease with which the target protein is associated.

As used herein, the term "genetic construct" refers to the DNA or RNA molecules that comprise a nucleotide sequence which encodes a target protein or immunomodulating protein. The coding sequence includes initiation and termination signals operably linked to regulatory elements including a promoter and polyadenylation signal capable of directing expression in the cells of the individual to whom the nucleic acid molecule is administered.

As used herein, the term "expressible form" refers to gene constructs that contain the necessary regulatory elements operable linked to a coding sequence that encodes a target protein or an immunomodulating protein, such that when present in the cell of the individual, the coding sequence will be expressed.

As used herein, the term "sharing an epitope" refers to proteins that comprise at least one epitope that is identical to or substantially similar to an epitope of another protein.

As used herein, the term "substantially similar epitope" is meant to refer to an epitope that has a structure that is not identical to an epitope of a protein but nonetheless invokes a cellular or humoral immune response that cross-reacts to that protein.

As used herein, the term "intracellular pathogen" is meant to refer to a virus or pathogenic organism that, at least part of its reproductive or life cycle, exists within a host cell and therein produces or causes to be produced, pathogen proteins.

As used herein, the term "hyperproliferative diseases" is meant to refer to those diseases and disorders characterized by hyperproliferation of cells.

As used herein, the tam "hyperproliferative-associated protein" is meant to refer to proteins that are associated with a hyperproliferative disease.

The invention arises from the discovery that when delivered as part of a vaccine, each of Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof, and combinations thereof modulates immune responses. Accordingly, a combination of these proteins may be delivered as immunotherapeutics in combination with or as components of a vaccine.

The GENBANK Accession number for the nucleotide sequence for Fos is K00650 or V01512, which are each incorporated herein by reference.

The GENBANK Accession number for the nucleotide sequence for c-jun J04111 or M29039, which are each incorporated herein by reference.

The GENBANK Accession number for the nucleotide sequence for Sp-1 is BC021101, BC005250, BC002878, M31126, J02893 or X15102, which are each incorporated herein by reference.

The nucleotide sequence for Ap1 can be identified as described in Lee et al, 1987 Cell 49:741-752, Rauscher et al. 1988 Science 240:1010-1016, and Chiu et al, 1988 Cell 54:541-552, which are each incorporated herein by reference.

The GENBANK Accession number for the nucleotide sequence for Ap-2 is M36711, which is incorporated herein by reference.

The GENBANK Accession number for the nucleotide sequence for p38 is U66243, which is incorporated herein by reference.

The GENBANK Accession number for the nucleotide sequence for p65Rel is L19067, which is incorporated herein by reference.

The GENBANK Accession number for the nucleotide sequence for MyD88 is U70451, which is incorporated herein by reference.

The GENBANK Accession number for the nucleotide sequence for IRAK is NM001569, which is incorporated herein by reference.

The GENBANK Accession number for the nucleotide sequence for TRAF6 is U78798, which is incorporated herein by reference.

The nucleotide sequence for IkB can be found as described in Gilmore et al. Trends Genet 1993 December; 9(12):427-33, which is incorporated herein by reference.

The GENBANK Accession number for the nucleotide sequence for NIK is Y10256, which is incorporated herein by reference.

The nucleotide sequence for SAP K can be found as described in Franklin et al. Oncogene. 1995, Dec. 7; 11(11): 2365-74. which is incorporated herein by reference.

The GENBANK Accession number for the nucleotide sequence for SAP1 is M85164 or M85165, which are each incorporated herein by reference.

The GENBANK Accession number for the nucleotide sequence for JNK2 is L31951, which is incorporated herein by reference.

The GENBANK Accession number for the nucleotide sequence for JNK1B2 is U35005; which is incorporated herein by reference.

The GENBANK Accession number for the nucleotide sequence for JNK1B1 is U35004; which is incorporated herein by reference.

The GENBANK Accession number for the nucleotide sequence for JNK2B2 is U35003; which is incorporated herein by reference.

The GENBANK Accession number for the nucleotide sequence for JNK2B1 is U35002; which is incorporated herein by reference.

The GENBANK Accession number for the nucleotide sequence for JNK1A2 is U34822; which is incorporated herein by reference.

The GENBANK Accession number for the nucleotide sequence for JNK2A1 is U34821; which is incorporated herein by reference.

The GENBANK Accession number for the nucleotide sequence for JNK3A1 is U34820; which is incorporated herein by reference.

The GENBANK Accession number for the nucleotide sequence for JNK3A2 is U34819, which is incorporated herein by reference.

The GENBANK Accession number for the nucleotide sequence for NF-kappa-B2, p49 splice form is A57034, which is incorporated herein by reference.

The GENBANK Accession number for the nucleotide sequence for NF-kappa-B2, p100 splice form is A42024, which is incorporated herein by reference.

The GENBANK Accession number for the nucleotide sequence for NF-kappa-B2, p105 splice form is S17233, which is incorporated herein by reference.

The GENBANK Accession number for the nucleotide sequence for NF-kappa-B 50K chain precursor is A37867, which is incorporated herein by reference.

The nucleotide sequence for NFkB p50 is described in Meyer R., et al. (1991) Proc. Natl. Acad. Sci. USA 88(3), 966 970, which is incorporated herein by reference.

Examples of interferon response genes includes those such as GENBANK Accession number M82819, GENBANK Accession number M81750 and GENBANK Accession number X02530, which are each incorporated herein by reference.

The GENBANK Accession number for the nucleotide and amino acid sequences for Bax is L22473, which is incorporated herein by reference.

The GENBANK Accession number for the nucleotide and amino acid sequences for TRAIL is U37518 or AF023849, which are incorporated herein by reference.

The GENBANK Accession number for the nucleotide and amino acid sequences for TRAILrecDRC5 is U90875 or AF016266, which are incorporated herein by reference. Also incorporated by reference are TRAIL-R2 AF016849; TRAIL-R3 AF014794; and TRAIL-R4 AF021232.

The GENBANK Accession number for the nucleotide and amino acid sequences for RANK is AF018253 which is incorporated herein by reference.

The GENBANK Accession number for the nucleotide and amino acid sequences for RANK LIGAND is AF019047 or AF333234, which are incorporated herein by reference.

The GENBANK Accession number for the nucleotide and amino acid sequences for Ox40 is X75962, which is incorporated herein by reference.

The GENBANK Accession number for the nucleotide and amino acid sequences for Ox40 LIGAND is X79929 or AB007839, which are incorporated herein by reference.

The GENBANK Accession number for the nucleotide and amino acid sequences for CD30 is M83554, (Durkop, H et al. Cell 68 (3), 421-427 (1992)) which is incorporated herein by reference.

The GENBANK Accession number for the nucleotide and amino acid sequences for CD153 (CD30L) is L09753, (Smith, C. A., et al. Cell 73 (7), 1349-1360 (1993)) which are incorporated herein by reference.

The GENBANK Accession number for the nucleotide and amino acid sequences for NKG2D is AF461811 or X54870, which are incorporated herein by reference.

The GENBANK Accession number for the nucleotide and amino acid sequences for MICA is X92841, which is incorporated herein by reference.

The GENBANK Accession number for the nucleotide and amino acid sequences for MICB is U65416, which is incorporated herein by reference.

The GENBANK Accession number for the nucleotide and amino acid sequences for NKG2A is X54867, which is incorporated herein by reference.

The GENBANK Accession number for the nucleotide and amino acid sequences for NKG2B is X54868, which is incorporated herein by reference.

The GENBANK Accession number for the nucleotide and amino acid sequences for NKG2C is X54869 or Aj0016984, which are incorporated herein by reference.

The GENBANK Accession number for the nucleotide and amino acid sequences for NKG2E is L14542, which is incorporated herein by reference.

The GENBANK Accession number for the nucleotide and amino acid sequences for NKG2F is AH006173, U96845 or U96846, which are incorporated herein by reference.

GENBANK Accession numbers for nucleotide sequences encoding TAP1 from various organisms are NC003070, NM000593, AY078409, NM105729, BM490855, NT007592, XM042533, BM427494, BM427300, AF363579, NM019828, NM013683, AF374376, NC000919, BM180265, AY034033, L76470, BI966112, AF130460, AF130459, L76469, L76468, BI390814, AB046578, BC003931, AF049342, AX113713, AX113705, AL132825, AJ297383, G67678, AF000999, BG148575, BG057675, BG056280, AC010796, AC011663, AE005173, AF306656, BF452070, BF452060, BF226195, BF222252, U60018, BE858232, BE852674, AB045382, AB045381, BB422079, BB387654, BB255358, BB245516, AF130458, AL023516, AF001156, AF001154, AF122909, AF108387, AF108386, AJ133720, AF115536, Z22935, AF072133, X97611, X66401, S63739, AH007357, AH007356, S70277, S70274, S70266, S70260, S70256, AE001245, X76125, X87344, AF029230, AF001003, AF001002, AF001001, AF001000, AF074420, L21208, L21207, L21206, L21205, L21204, AF027865, Z83327, U07198, U07197, L11145, U60023, U60022, U60021, U60020, U60019, Y10235, Y10234, Y10233, Y10232, Y10231, Y10230, S61567, X15853, X57295, X57296, X76126, U16763, and A26291, which are incorporated herein by reference.

GENBANK Accession numbers for nucleotide sequences encoding TAP2 from various organisms are AY078410, AF318024, BM507982, BM502957, BM490914, NT007592, XM057393, AB073378, BM440229, BM440091, BM427137, BM426919, BM426349, BM426032, AB073376, AF363580, NM011530, BM183904, BM183583, AB007195, AB073779, AF032394, AF415199, AB033382, U23449, B1066980, NM032056, BG710769, AX113714, AX113706, AF105151, NM018833, NM000544, BG625266, BG347134, BG146728, AF307513, AF307512, BF460450, BF152529, BF146508, AY007425, BE192109, BE508441, BE508152, BE507783, BE192407, AB045382, AB045381, BE447094, BE027078, BE026341, BE025973, AW765923, AW765500, D78570, D42066, AJ251484, AJ251485, AW324451, AW228188, AL023516, AF001157, AF001155, AH008290, AF097679, AF097678, AF097677, AF097676, AF097675, AF097674, AF097673, AF097672, AF097671, AF097670, AF097699, AF108385, AF115538, AF115537, AF110317, AF002180, AF176984, Z22936, Z22935, AF152583, AF078671, AI664100, AI663762, AH007567, AF136750, AF136749, AF136748, AF136747, AH007554, AF100418, AF100417, AF100416, AF100415, X66401, AF062387, X87344, AF077421, AF027865, AA565145, AA543885, U60090, U60089, U60088, U60087, U60092, U60091, L49032, L49035, L49034, L49033, S78269, X15854, X55434, X75307, X75306, X75305, U07844, R89692, A26220, L10287, L09191, L09271, and Z28380, which are incorporated herein by reference.

According to some embodiments of the invention, the combination of an immunogen and one or more transcription factors selected from the group consisting of: Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof is delivered to an individual to modulate the activity of the individual's immune system and thereby enhance the immune response against the immunogen. When the nucleic acid molecules that encode the transcription factors are taken up by cells of the individual the nucleotide sequences that encode the transcription factors are expressed in the cells and the proteins are thereby delivered to the individual. Aspects of the invention provide methods of delivering the coding sequences of the proteins on a single nucleic acid molecule, in compositions comprising different nucleic acid molecules that encodes one or more of the various transcription factors, as part of recombinant vaccines and as part of attenuated vaccines.

According to some aspects of the present invention, compositions and methods are provided which prophylactically and/or therapeutically immunize an individual against a pathogen or abnormal, disease-related cells. The vaccine may be any type of vaccine such as, a live attenuated vaccine, a cell vaccine, a recombinant vaccine or a nucleic, acid or DNA vaccine. By delivering nucleic acid molecules that encode an immunogen and one or more of Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof the immune response induced by the vaccine may be modulated.

Isolated cDNA that encodes the immunomodulating proteins are useful as a starting material in the construction of constructs that can produce that immunomodulating protein. Using standard techniques and readily available starting materials, a nucleic acid molecule that encodes an immunomodulating protein may be prepared.

The present invention relates to compositions for delivering the immunomodulating proteins and methods of using the same. Aspects of the present invention relate to nucleic acid molecules that comprise a nucleotide sequence that encodes one or more of Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof operably linked to regulatory elements in combination with a nucleotide sequence that encodes an immunogen operably linked to regulatory elements. Aspects of the present invention relate to compositions which comprise a nucleic acid molecule that comprises a nucleotide sequence that encodes one or more of Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof operably linked to regulatory elements in combination with a nucleic acid molecule that comprises a nucleotide sequence that encodes an immunogen operably linked to regulatory elements. The present invention further relates to injectable pharmaceutical compositions that comprise such nucleic acid molecules.

The nucleic acid molecules may be delivered using any of several well known technologies including DNA injection (also referred to as DNA vaccination), recombinant vectors such as recombinant adenovirus, recombinant adenovirus associated virus and recombinant vaccinia.

DNA vaccines are described in U.S. Pat. Nos. 5,593,972, 5,739,118, 5,817,637, 5,830,876, 5,962,428, 5,981,505, 5,580,859, 5,703,055, 5,676,594, and the priority applications cited therein, which are each incorporated herein by reference. In addition to the delivery protocols described in those applications, alternative methods of delivering DNA are described in U.S. Pat. Nos. 4,945,050 and 5,036,006, which are both incorporated herein by reference.

Routes of administration include, but are not limited to, intramuscular, intransally, intraperitoneal, intradermal, subcutaneous, intravenous, intraarterially, intraoccularly and oral as well as topically, transdermally, by inhalation or suppository or to mucosal tissue such as by lavage to vaginal, rectal, urethral, buccal and sublingual tissue. Preferred routes of administration include to mucosal tissue, intramuscular, intraperitoneal, intradermal and subcutaneous injection. Genetic constructs may be administered by means including, but not limited to, traditional syringes, needleless injection devices, or "microprojectile bombardment gone guns".

When taken up by a cell, the genetic construct(s) may remain present in the cell as a. functioning extracbromosomal molecule and/or integrate into the cell's chromosomal DNA. DNA may be introduced into cells where it remains as separate genetic material in the form of a plasmid or plasmids. Alternatively, linear DNA that can integrate into the chromosome may be introduced into the cell. When introducing DNA into the cell, reagents that promote DNA integration into chromosomes may be added. DNA sequences that are useful to promote integration may also be included in the DNA molecule. Alternatively, RNA may be administered to the cell. It is also contemplated to provide the genetic construct as a linear minichromosome including a centromere, telomeres and an origin of replication. Gene constructs may remain part of the genetic material in attenuated live microorganisms or recombinant microbial vectors which live in cells. Gene constructs may be part of genomes of recombinant viral vaccines where the genetic material either integrates into the chromosome of the cell or remains extrachromosomal. Genetic constructs include regulatory elements necessary for gene expression of a nucleic acid molecule. The elements include: a promoter, an initiation codon, a stop codon, and a polyadenylation signal. In addition, enhancers are often required for gene expression of the sequence that encodes the target protein or the immunomodulating protein. It is necessary that these elements be operable linked to the sequence that encodes the desired proteins and that the regulatory elements are operably in the individual to whom they are administered.

Initiation codons and stop codon are generally considered to be part of a nucleotide sequence that encodes the desired protein. However, it is necessary that these elements are functional in the individual to whom the gene construct is administered. The initiation and termination codons must be in frame with the coding sequence.

Promoters and polyadenylation signals used must be functional within the cells of the individual.

Examples of promoters useful to practice the present invention, especially in the production of a genetic vaccine for humans, include but are not limited to promoters from Simian Virus 40 (SV40), Mouse Mammary Tumor Virus (MMTV) promoter, Human Immunodeficiency Virus (MV) such as the BIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metalothionein.

Examples of polyadenylation signals useful to practice the present invention, especially in the production of a genetic vaccine for humans, include but are not limited to SV40 polyadenylation signals and LTR polyadenylation signals. In particular, the SV40 polyadenylation signal that is in pCEP4 plasmid (Invitrogen, San Diego Calif.), referred to as the SV40 polyadenylation signal, is used.

In addition to the regulatory elements required for DNA expression, other elements may also be included in the DNA molecule. Such additional elements include enhancers. The enhancer may be selected from the group including but not limited to: human Actin, human Myosin, human Hemoglobin, human muscle creatine and viral enhancers such as those from CMV, RSV and EBV.

Genetic constructs can be provided with mammalian origin of replication in order to maintain the construct extrachromosomally and produce multiple copies of the construct in the cell. Plasmids pVAX1, pCEP4 and pREP4 from Invitrogen (San Diego, Calif.) contain the Epstein Barr virus origin of replication and nuclear antigen EBNA-1 coding region which produces high copy episomal replication without integration.

In some preferred embodiments related to immunization applications, nucleic acid molecule(s) are delivered which include nucleotide sequences that encode a target protein, the immunomodulating protein and, additionally, genes for proteins which further enhance the immune response against such target proteins. Examples of such genes are those which encode other cytokines and lymphokines such as alpha-interferon, gamma-interferon, platelet derived growth factor (PDGF), TNF, GM-CSF, epidermal growth factor (EGF), IL-1, IL-2, II-4, IL-6, IL-10, IL-12 and IL-15 including IL-15 having the signal sequence deleted and optionally including the signal peptide from IgE.

An additional element may be added which serves as a target for cell destruction if it is desirable to eliminate cells receiving the genetic construct for any reason. A herpes thymidine kinase (tk) gene in an expressible form can be included in the genetic construct. The drug gangcyclovir can be administered to the individual and that drug will cause the selective killing of any cell producing tk, thus, providing the means for the selective destruction of cells with the genetic construct.

In order to maximize protein production, regulatory sequences may be selected which are well suited for gene expression in the cells the construct is administered into. Moreover, codons may be selected which are most efficiently transcribed in the cell. One having ordinary skill in the art can produce DNA constructs that are functional in the cells.

In some embodiments, gene constructs may be provided to in order to produce coding sequences for the immunomodulatory proteins described herein linked to IgE signal peptide.

One method of the present invention comprises the steps of administering nucleic acid molecules intramuscularly, intranasally, intraperatoneally, subcutaneously, intradermally, or topically or by lavage to mucosal tissue selected from the group consisting of inhalation, vaginal, rectal, urethral, buccal and sublingual.

In some embodiments, the nucleic acid molecule is delivered to the cells in conjunction with administration of a polynucleotide function enhancer or a genetic vaccine facilitator agent. Polynucleotide function enhancers are described in U.S. Pat. Nos. 5,593,972, 5,962,428 and International Application Serial Number PCT/US94/00899 filed Jan. 26, 1994, which are each incorporated herein by reference. Genetic vaccine facilitator agents are described in U.S. Ser. No. 021,579 filed Apr. 1, 1994, which is incorporated herein by reference. The co-agents that are administered in conjunction with nucleic acid molecules may be administered as a mixture with the nucleic acid molecule or administered separately simultaneously, before or after administration of nucleic acid molecules. In addition, other agents which may function transfecting agents and/or replicating agents and/or inflammatory agents and which may be co-administered with a GVF include growth factors, cytokines and lymphokines such as a-interferon, gamma-interferon, GM-CSF, platelet derived growth factor (PDGF), TNF, epidermal growth factor (EGF), IL-1, IL-2, IL-4, IL-6, IL-10, IL-12 and IL-15 as well as fibroblast growth factor, surface active agents such as immune-stimulating complexes (ISCOMS), Freunds incomplete adjuvant, LPS analog including monophosphoryl Lipid A (WL), muramyl peptides, quinone analogs and vesicles such as squalene and squalene, and hyaluronic acid may also be used administered in conjunction with the genetic construct In some embodiments, an immunomodulating protein may be used as a GVF. In some embodiments, the nucleic acid molecule is provided in association with PLG to enhance delivery/uptake.

The pharmaceutical compositions according to the present invention comprise about 1 nanogram to about 2000 micrograms of DNA. In some preferred embodiments, pharmaceutical compositions according to the present invention comprise about 5 nanogram to about 1000 micrograms of DNA. In some preferred embodiments, the pharmaceutical compositions contain about 10 nanograms to about 800 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms of DNA. In some preferred embodiments, the pharmaceutical compositions contain about 100 to about 200 microgram DNA.

The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

According to some embodiments of the invention, methods of inducing immune responses against an immunogen are provided by delivering a combination of the immunogen and one or more of Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof to an individual. The vaccine may be a live attenuated vaccine, a cell vaccine, a recombinant vaccine or a nucleic acid or DNA vaccine.

The present invention is useful to elicit enhanced immune responses against a target protein, i.e. proteins specifically associated with pathogens, allergens or the individual's own "abnormal" cells. The present invention is useful to immunize individuals against pathogenic agents and organisms such that an immune response against a pathogen protein provides protective immunity against the pathogen. The present invention is useful to combat hyperproliferative diseases and disorders such as cancer by eliciting an immune response against a target protein that is specifically associated with the hyperproliferative cells. The present invention is useful to combat autoimmune diseases and disorders by eliciting an immune response against a target protein that is specifically associated with cells involved in the autoimmune condition.

According to some aspects of the present invention, DNA or RNA that encodes a target protein and immunomodulating proteins is introduced into the cells of tissue of an individual where it is expressed, thus producing the encoded proteins. The DNA or RNA sequences encoding the target protein and one or both immunomodulating proteins are linked to regulatory elements necessary for expression in the cells of the individual. Regulatory elements for DNA expression include a promoter and a polyadenylation signal. In addition, other elements, such as a Kozak region, may also be included in the genetic construct.

In some embodiments, expressible forms of sequences that encode the target protein and expressible forms of sequences that encode both immunomodulating proteins are found on the same nucleic acid molecule that is delivered to the individual.

In some embodiments, expressible forms of sequences that encode the target protein occur on a separate nucleic acid molecule from the nucleic acid molecules that contain expressible forms of sequences that encode one or more immunomodulatory proteins. In some embodiments, expressible forms of sequences that encode the target protein and expressible forms of sequences that encode one or more of the immunomodulatory proteins occur on a one nucleic acid molecule that is separate from the nucleic acid molecule that contain expressible forms of sequences that encode one or more of the immunomodulating proteins. Multiple different nucleic acid molecules can be produced and delivered according to the present invention and delivered to the individual. For example, in some embodiments, expressible forms of sequences that encode the target protein occur on separate nucleic acid molecule from the nucleic acid molecules that contain expressible forms of sequences that encode one or more of the two immunomodulating proteins which occur on separate nucleic acid molecule from the nucleic acid molecules that contain expressible forms of sequences that encode one or more immunomodulating proteins. In such cases, all three molecules are delivered to the individual.

The nucleic acid molecule(s) may be provided as plasmid DNA, the nucleic acid molecules of recombinant vectors or as part of the genetic material provided in an attenuated vaccine or cell vaccine. Alternatively, in some embodiments, the target protein and/or wither or both immunomodulating proteins maybe delivered as a protein in addition to the nucleic acid molecules that encode them or instead of the nucleic acid molecules which encode them.

Genetic constructs may comprise a nucleotide sequence that encodes a target protein or an immunomodulating protein operably linked to regulatory elements needed for gene expression. According to the invention, combinations of gone constructs that include one that comprises an expressible form of the nucleotide sequence that encodes a target protein and one that includes an expressible form of the nucleotide sequence that encodes an immunomodulating protein are provided. Incorporation into a living cell of the DNA or RNA molecule(s) that include the combination of gene constructs results in the expression of the DNA or RNA and production of the target protein and one or more immunomodulating proteins. An enhanced immune response against the target protein results.

The present invention may be used to immunize an individual against all pathogens such as viruses, prokaryote and pathogenic eukaryotic organisms such as unicellular pathogenic organisms and multicellular parasites. The present invention is particularly useful to immunize an individual against those pathogens which infect cells and which are not encapsulated such as viruses, and prokaryote such as gonorrhea, listeria and shigella. In addition, the present invention is also useful to immunize an individual against protozoan pathogens that include a stage in the life cycle where they are intracellular pathogens. Table 1 provides a listing of some of the viral families and genera for which vaccines according to the present invention can be made. DNA constructs that comprise DNA sequences that encode the peptides that comprise at least an epitope identical or substantially similar to an epitope displayed on a pathogen antigen such as those antigens listed on the tables are useful in vaccines. Moreover, the present invention is also useful to immunize an individual against other pathogens including prokaryotic and eukaryotic protozoan pathogens as well as multicellular parasites such as those listed on Table 2.

In order to produce a genetic vaccine to protect against pathogen infection, genetic material that encodes immunogenic proteins against which a protective immune response can be mounted must be included in a genetic construct as the coding sequence for the target. Whether the pathogen infects intracellularly, for which the present invention is particularly useful, or extracellularly, it is unlikely that all pathogen antigens will elicit a protective response. Because DNA and RNA are both relatively small and can be produced relatively easily, the present invention provides the additional advantage of allowing for vaccination with multiple pathogen antigens. The genetic construct used in the genetic vaccine can include genetic material that encodes many pathogen antigens. For example, several viral genes may be included in a single construct thereby providing multiple targets.

Tables 1 and 2 include lists of some of the pathogenic agents and organisms for which genetic vaccines can be prepared to protect an individual from infection by them. In some preferred embodiments, the methods of immunizing an individual against a pathogen are directed against HIV, HSV, HCV, WNV or HBV.

Another aspect of the present invention provides a method of conferring a protective immune response against hyperproliferating cells that are characteristic in hyperproliferative diseases and to a method of treating individuals suffering from hyperproliferative diseases. Examples of hyperproliferative diseases include all forms of cancer and psoriasis.

It has been discovered that introduction of a genetic construct that includes a nucleotide sequence which encodes—an immunogenic "hyperproliferating cell"—associated protein into the cells of an individual results in the production of those proteins in the vaccinated cells of an individual. To immunize against hyperproliferative diseases, a genetic construct that includes a nucleotide sequence that encodes a protein that is associated with a hyperproliferative disease is administered to an individual.

In order for the hyperproliferative-associated protein to be an effective immunogenic target, it must be a protein that is produced exclusively or at higher levels in hyperproliferative cells as compared to normal cells. Target antigens include such proteins, fragments thereof and peptides; which comprise at least an epitope found on such proteins. In some cases, a hyperproliferative-associated protein is the product of a mutation of a gene that encodes a protein. The mutated gene encodes a protein that is nearly identical to the normal protein except it has a slightly different amino acid sequence which results in a different epitope not found on the normal protein. Such target proteins include those which are proteins encoded by oncogenes such as myb, myc, fyn, and the translocation gene bcr/abl, ras, src, P53, neu, trk and EGRF. In addition to oncogene products as target antigens, target proteins for anticancer treatments and protective regimens include variable regions of antibodies made by B cell lymphomas and variable regions of T cell receptors of T cell lymphomas which, in some embodiments, are also used target antigens for autoimmune disease. Other tumor-associated proteins can be used as target proteins such as proteins that are found at higher levels in tumor cells including the protein recognized by monoclonal antibody 17-IA and folate binding proteins or PSA.

While the present invention may be used to immunize an individual against one or more of several forms of cancer, the present invention is particularly useful to prophylactically immunize an individual who is predisposed to develop a particular cancer or who has had cancer and is therefore susceptible to a relapse. Developments in genetics and technology as well as epidemiology allow for the determination of probability and risk assessment for the development of cancer in individual. Using genetic screening and/or family health histories, it is possible to predict the probability a particular individual has for developing any one of several types of cancer.

Similarly, those individuals who have already developed cancer and who have been treated to remove the cancer or are otherwise in remission are particularly susceptible to relapse and reoccurrence. As part of a treatment regimen, such individuals can be immunized against the cancer that they have been diagnosed as having had in order to combat a recurrence. Thus, once it is known that an individual has had a type of cancer and is at risk of a relapse, they can be immunized in order to prepare their immune system to combat any future appearance of the cancer.

The present invention provides a method of treating individuals suffering from hyperproliferative diseases. In such methods, the introduction of genetic constructs serves as an immunotherapeutic, directing and promoting the immune system of the individual to combat hyperproliferative cells that produce the target protein.

The present invention provides a method of treating individuals suffering from autoimmune diseases and disorders by conferring a broad based protective immune response against targets that are associated with autoimmunity including cell receptors and cells which produce "self"-directed antibodies.

T cell mediated autoimmune diseases include Rheumatoid arthritis (RA), multiple sclerosis (MS), Sjogren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors that bind to endogenous antigens and initiate the inflammatory cascade associated with autoimmune diseases. Vaccination against the variable region of the T cells would elicit an immune response including CTLs to eliminate those T cells.

In RA, several specific variable regions of T cell receptors (TCRs) that are involved in the disease have been characterized. These TCRs include Vβ-3, Vβ-14, 20 Vβ-17 and Va-17. Thus, vaccination with a DNA construct that encodes at least one of these proteins will elicit an immune response that will target T cells involved in RA. See: Howell, M. D., et al., 1991 *Proc. Nat. Acad. Sci. USA* 88:10921-10925; Piliard, X., et al, 1991 *Science* 253:325-329; Williams, W. V., et al., 1992 *J Clin. Invest.* 90:326-333; each of which is incorporated herein by reference. In MS, several specific variable regions of TCRs that are involved in the disease have been characterized. These TCRs include VfP and Va-10. Thus, vaccination with a DNA construct that encodes at least one of these proteins will elicit an immune response that will target T cells involved in MS. See: Wucherpfennig, K. W., et al., 1990 *Science* 248: 1016-1019; Oksenberg, J. R., et al, 1990 *Nature* 345:344-346; each of which is incorporated herein by reference.

In scleroderma, several specific variable regions of TCRs that are involved in the disease have been characterized. These TCRs include Vβ-6, Vβ-8, Vβ-14 and Va-16, Va-3C, Va-7, Va-14, Va-15, Va-16, Va-28 and Va-12. Thus, vaccination with a DNA construct that encodes at least one of these proteins will elicit an immune response that will target T cells involved in scleroderma.

In order to treat patients suffering from a T cell mediated autoimmune disease, particularly those for which the variable region of the TCR has yet to be characterized, a synovial biopsy can be performed. Samples of the T cells present can be taken and the variable region of those TCRs identified using standard techniques. Genetic vaccines can be prepared using this information.

B cell mediated autoimmune diseases include Lupus (SLE), Grave's disease, myasthenia gravis, autoimmune hemolytic anemia, autoimmune thrombocytopenia, asthma, cryoglobulinemia, primary biliary sclerosis and pernicious anemia. Each of these diseases is characterized by antibodies that bind to endogenous antigens and initiate the inflammatory cascade associated with autoimmune diseases. Vaccination against the variable region of antibodies would elicit an immune response including CTLs to eliminate those B cells that produce the antibody.

In order to treat patients suffering from a B cell mediated autoimmune disease, the variable region of the antibodies involved in the autoimmune activity must be identified. A biopsy can be performed and samples of the antibodies present at a site of inflammation can be taken. The variable region of those antibodies can be identified using standard techniques. Genetic vaccines can be prepared using this information.

In the case of SLE, one antigen is believed to be DNA. Thus, in patients to be immunized against SLE, their sera can be screened for anti-DNA antibodies and a vaccine can be prepared which includes DNA constructs that encode the variable region of such anti-DNA antibodies found in the sera.

Common structural features among the variable regions of both TCRs and antibodies are well known. The DNA sequence encoding a particular TCR or antibody can generally be found following well known methods such as those described in Kabat, et al 1987 *Sequence of Proteins of Immunological Interest* U.S. Department of Health and Human Services, Bethesda Md., which is incorporated herein by reference. In addition, a general method for cloning functional variable regions from antibodies can be found in Chaudhary, V. K., et al, 1990 *Proc. Natl. Acad Sci. USA* 87:1066, which is incorporated herein by reference.

In addition to using expressible forms of immunomodulating protein coding sequence to improve genetic vaccines, the present invention relates to improved attenuated live vaccines and improved vaccines that use recombinant vectors to deliver foreign genes that encode antigens. Examples of attenuated live vaccines and those using recombinant vectors to deliver foreign antigens are described in U.S. Pat. Nos. 4,722,848; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; and 5,482,713, which are each incorporated herein by reference. Gene constructs are provided which include the nucleotide sequence that encodes an immunomodulating protein is operably linked to regulatory sequences that can function in the vaccine to effect expression. The gene constructs are incorporated in the attenuated live vaccines and recombinant vaccines to produce improved vaccines according to the invention.

The present invention provides an improved method of immunizing individuals that comprises the step of delivering gene constructs to the cells of individuals as part of vaccine compositions which include are provided which include DNA vaccines, attenuated live vaccines and recombinant vaccines. The gene constructs comprise a nucleotide sequence that encodes an immunomodulating protein and that is operably linked to regulatory sequences that can function in the vaccine to effect expression. The improved vaccines result in an enhanced cellular immune response.

Example

Plasmid-Encoded OX40 as a Molecular Adjuvant in DNA Vaccination

Enhancing Humoral Immune Responses

The OX40/OX40L pathway has been shown to be an important part of priming dendritic cells to drive a Th2 immune response and polarizing recently activated CD4+ T cells toward a Th2 phenotype.

Data show that the resulting immune response is primarily a significant antibody response when a DNA vaccine construct is provided in which an expressible form of DNA encoding the death domain OX40 is included with a DNA construct that encodes an expressible form of DNA encoding an immunogen. These results, which indicate that the presence of OX40 in vaccinated cells can interact with the OX40 receptor which is found on B cells, are surprising. Enhanced antibody and CD4+ responses seen with coadministration of plasmid encoded OX40 is indicated by the data shown in FIGS. 1 and 2. Enhanced antibody responses seen with coadministration of plasmid encoded OX40 is further indicated by the data shown in FIG. 3.

A "foreign antigen" forms a complex a B cell receptor that uniquely recognizes that foreign antigen. The complex then interacts with a helper T cells that recognizes the complex and responds by secreting messengers such as cytokines. The B cell responds to the secreted messengers by producing antibodies which specifically bind to the foreign antigen.

The DNA vaccine which was used in the present experiments included coding sequences form HIV env. This protein is not secreted but rather is primarily localized to the cell membrane of the cell that takes up the DNA vaccine plasmid and expresses the proteins encoded by the plasmid DNA. The DNA vaccine also contains OX40 coding sequences which are also expressed by the cells that take up the DNA vaccine plasmid.

In the absence of OX40, the DNA vaccine that encodes HIV env induces a minimal antibody response, presumably because no protein is secreted. CTL immune responses are generated against env. Surprisingly, the presence of OX40 results in a significant antibody response and a minimal CTL response. It is unclear how this change in immune response occurs, i.e what mechanism results in B cell involvement and shut down of CTL response. The practical applications of this discovery is that DNA vaccines can be designed to provide significant antibody responses. Antibody responses are needed in the protection and clearance against numerous pathogens such as hepatitis virus (HAV, HBV, HCV), dengivirus as well as in the protection and treatment against allergens. Moreover, DNA vaccines with suppressed CTL responses and significant antibody responses may be particularly useful in treating cancer and autoimmune diseases. Such vaccines generally provide sequences that encode cancer and autoimmune associated proteins which are generally self proteins preferentially expressed on cells associated with the disease. The absence of a CTL response will minimize the possibility of inducing an undesirable autoimmune response while still providing an immune response that can attack undesirable cells. Accordingly, constructs and compositions which provide OX40 coding sequences in combination with coding sequences for pathogen antigens, allergens, antigens associated with hyperproliferative diseases and antigens from cells associated with autoimmune diseases as described herein are particularly useful embodiments of the present invention.

TABLE 1

| | |
|---|---|
| Picornavirus Family | |
| Genera: | Rhinoviruses: (Medical) responsible for −50% cases of the common cold.<br>Etheroviruses: (Medical) includes polioviruses, coxsackieviruses, echoviruses, and human enteroviruses such as hepatitis A virus.<br>Apthoviruses: (Veterinary) these are the foot and mouth disease viruses. |
| Target antigens: | VP1, VP2, VP3, VP4, VPG |
| Calcivirus Family | |
| Genera: | Norwalk Group of Viruses: (Medical) these viruses, are an important causative agent of epidemic gastroenteritis. |
| Togavirus Family | |
| Genera: | Alphaviruses: (Medical and Veterinary) examples include Senilis viruses, RossRiver virus and Eastern & Western Equine encephalitis.<br>Reovirug: (Medical) Rubella virus. |
| Flariviridue Family | |
| | Examples include: (Medical) dengue, yellow fever, Japanese encephalitis, St. Louis encephalitis and tick borne encephalitis viruses. West Nile virus (Genbank NC001563, AF533540, AF404757, AF404756, AF404755, AF404754, AF404753, AF481864, M12294, AF317203, AF196835, AF260969, AF260968, AF260967, AF206518 and AF202541) |
| Representative Target antigens: | |
| | E<br>NS5<br>C |
| Hepatitis C Virus: (Medical) these viruses are not placed in a family yet but are believed to be either a togavirus or a flavivirus. Most similarity is with togavirus family. | |
| Coronavirus Family: (Medical and Veterinary) | |
| | Infectious bronchitis virus (poultry)<br>Porcine transmissible gastroenteric virus (pig)<br>Porcine hemaglutinating encephalomyelitis virus (pig)<br>Feline infectious peritonitis virus (cats)<br>Feline enteric coronavirus (cat)<br>Canine coronavirus (dog)<br>SARS associated coronavirus<br>The human respiratory coronaviruses cause ~40 cases of common cold.<br>EX. 224E, OC43<br>Note - coronaviruses may cause non-A, B or C hepatitis |
| Target antigens: | El - also called M or matrix protein<br>E2 - also called S or Spike protein<br>E3 - also called BE or hemagglutin-elterose glycoprotein (not present in all coronaviruses)<br>N - nucleocapsid |
| Rhabdovirus Family | |
| Genera: | Vesiliovirus<br>Lyssavirus:(medical and veterinary) rabies |

TABLE 1-continued

| | |
|---|---|
| Target antigen: | G protein |
| | N protein |
| Filoviridue Family: (Medical) | |
| | Hemorrhagic fever viruses such as Marburg and Ebola virus |
| Paramyxovirus Family: | |
| Genera: | Paramyxovirus: (Medical and Veterinary) |
| | Mumps virus, New Castle disease virus (important pathogen in chickens) |
| | Morbillivirus: (Medical and Veterinary) |
| | Measles, canine distemper |
| | Pneuminvirus: (Medical and Veterinary) |
| | Respiratory syncytial virus |
| Orthomyxovirus Family (Medical) | |
| | The Influenza virus |
| Bungavirus Family | |
| Genera: | Bungavirus: (Medical) California encephalitis, LA Crosse |
| | Phlebovirus: (Medical) Rift Valley Fever |
| | Hantavirus: Puremala is a hemahagin fever virus |
| | Nairvirus (Veterinary) Nairobi sheep disease |
| | Also many unassigned bungaviruses |
| Arenavirus Family (Medical) | |
| | LCM, Lassi fever virus |
| Reovirus Family | |
| Genera: | Reovirus: a possible human pathogen |
| | Rotavirus: acute gastroenteritis in children |
| | Orbiviruses: (Medical and Veterinary) |
| | Colorado Tick fever, Lebombo (humans) equine encephalosis, blue tongue |
| Retroyirus Family | |
| Sub-Family: | Oncorivirinal: (Veterinary) (Medical) feline leukemia virus, HTLVI and HTLVII |
| | Lentivirinal: (Medical and Veterinary) HIV, feline immunodeficiency virus, equine infections, anemia virus |
| | Spumavirinal |
| Papovavirus Family | |
| Sub-Family: | Polyomaviruses: (Medical) BKU and JCU viruses |
| Sub-Family: | Papillomavirus: (Medical) many viral types associated with cancers or malignant progression of papilloma. |
| Adenovirus (Medical) | |
| | EX AD7, ARD., O.B. - cause respiratory disease - some adenoviruses such as 275 cause enteritis |
| Parvovirus Family (Veterinary) | |
| | Feline parvovirus: causes feline enteritis |
| | Feline panleucopeniavirus |
| | Canine parvovirus |
| | Porcine parvovirus |
| Herpesvirus Family | |
| Sub-Family: | alphaherpesviridue |
| Genera: | Simplexvirus (Medical) |
| | HSVI (Genbank X14112, NC001806), HSVII (NC001798) |
| | Varicellovinis: (Medical Veterinary) pseudorabies - varicella zoster |
| Sub-Family - | betaherpesviridue |
| Genera: | Cytomegalovirus (Medical) |
| | HCMV |
| | Muromegalovirus |
| Sub-Family. | Gammaherpesviridue |
| Genera: | Lymphocryptovirus (Medical) |
| | EBV - (Burkitts lympho) |
| | Rhadinovirus |
| Poxvirus Family | |
| Sub-Family | Chordopoxviridue (Medical - Veterinary) |
| Genera: | Variola. (Smallpox) |
| | Vaccinia (Cowpox) |
| | Parapoxivirus - Veterinary |
| | Auipoxvirus - Veterinary |
| | Capripoxvirus |

TABLE 1-continued

| | Leporipoxvirus |
| | Suipoxviru's |
| Sub-Family: | Entemopoxviridue |
| Hepadnavirus Family | |
| | |
| | Hepatitis B virus |
| Unclassified | Hepatitis delta virus |

TABLE 2

| Bacterial pathogens | Pathogenic gram-positive cocci include: pneumococcal; staphylococcal; and streptococcal. Pathogenic gram-negative cocci include: meningococcal; and gonococcal.<br>Pathogenic enteric gram-negative bacilli include: enterobacteriaceae; pseudomonas, acinetobacteria and eikenella, melioidosis;,sahnonella; shigellosis; hemophilus; chancroid; brucellosis; tularemia; yersinia (pasteurella); streptobacillus mortiliformis and spirillum; listeria monocytogenes; erysipelothrix rhusiopathiae; diphtheria, cholera, anthrax; donovanosis (granuloma inguinale); and bartonellosis.<br>Pathogenic anaerobic bacteria include: tetanus; botulism; other clostridia; tuberculosis; leprosy; and other mycobacteria. Pathogenic spirochetal diseases include: syphilis; - treponematoses: yaws, pinta and endemic syphilis; and leptospirosis.<br>Other infections caused by higher pathogen bacteria and pathogenic fungi include: actinomycosis;.nocardiosis; cryptococcosis, blastomycosis, histoplasmosis and coccidioidomycosis; candidiasis, aspergillosis, and mucormycosis; sporotrichosis, paracoccidiodomycosis, petriellidiosis, torulopsosis, mycetoma, and chromomycosis; and dermatophytosis.<br>Rickettsial infections include rickettsial and rickettsioses.<br>Examples of mycoplasma and chlamydial infections include: mycoplasma pneumoniae; lymphogranuloma venereum; psittacosis; and perinatal chlamydial infections. |
| Pathogenic eukaryotes | Pathogenic protozoans and helminths and infections thereby include: amebiasis; malaria; leishmaniasis; trypanosomiasis; toxoplasmosis; pneumocystis carinii; babesiosis; giardiasis; trichinosis; filariasis; schistosomiasis; nematodes; trematodes or flukes; and cestode (tapeworm) infections. |

The invention claimed is:

1. A composition comprising:
an isolated nucleic acid molecule that encodes an immunogen, wherein said immunogen is a pathogen antigen, and
an isolated nucleic acid molecule that encodes Ox40,
wherein the isolated nucleic acid sequence that encodes the immunogen occurs on a separate nucleic acid molecule from the nucleic acid sequence that Ox40.

2. The composition of claim 1 wherein said nucleic acid molecules are plasmids.

3. The composition of claim 1 wherein said immunogen is a herpes simplex antigen.

4. The composition of claim 3 wherein said herpes simplex antigen is HSV2gD.

5. An injectable pharmaceutical composition comprising the composition of claim 1.

6. A method of inducing an immune response in an individual against an immunogen comprising administering to said individual a composition of claim 1.

* * * * *